United States Patent [19]

Tanokura et al.

[11] Patent Number: 4,976,851
[45] Date of Patent: Dec. 11, 1990

[54] LIQUID SEPARATOR

[75] Inventors: Nobukazu Tanokura; Susumu Fujikawa, both of Fujinomiya, Japan

[73] Assignee: Terumo Kabushiki Kaisha, Tokyo, Japan

[21] Appl. No.: 359,490

[22] Filed: May 31, 1989

[30] Foreign Application Priority Data

Jun. 6, 1988 [JP] Japan .................. 63-138625

[51] Int. Cl.$^5$ .................. B01D 21/36; B01D 21/30
[52] U.S. Cl. .................. 210/86; 210/94; 210/109; 210/143; 210/513; 222/23; 222/52; 222/96; 222/103; 222/214
[58] Field of Search .................. 210/85, 86, 94, 109, 210/143, 257.1, 513, 514, 515, 141, ; 222/95, 96, 52, 103, 214, 23

[56] References Cited

U.S. PATENT DOCUMENTS

| | | | |
|---|---|---|---|
| 2,903,161 | 9/1959 | Stahmer | 222/103 |
| 3,753,739 | 6/1968 | Noble | 210/513 |
| 4,040,959 | 8/1977 | Berman et al. | 210/516 |
| 4,284,209 | 8/1981 | Barbour Jr. | 222/103 |
| 4,350,585 | 9/1982 | Johansson et al. | 210/94 |
| 4,663,032 | 5/1987 | Loos et al. | 210/97 |

FOREIGN PATENT DOCUMENTS

| | | |
|---|---|---|
| 2136242 | 3/1972 | Fed. Rep. of Germany . |
| 55-17585 | 5/1980 | Japan . |
| 55-155652 | 12/1980 | Japan . |
| 57-30507 | 6/1982 | Japan . |
| 61-29363 | 2/1986 | Japan . |
| WO-A1-86/04829 | 8/1986 | PCT Int'l Appl. . |
| WO-A1-88/03418 | 5/1988 | PCT Int'l Appl. . |

Primary Examiner—W. Gary Jones
Attorney, Agent, or Firm—Frishauf, Holtz, Goodman & Woodward

[57] ABSTRACT

A liquid separator for use as a blood component separator separates a blood component such as blood plasma from centrifugally separated component layers in a flexible blood bag. The blood bag has a liquid discharge tube on its upper end. The liquid separator includes a container holder for holding the blood bag with the liquid discharge tube directed substantially upwardly, and a container presser for pressing the blood bag progressively from the upper end toward a lower end thereof in coaction with the container holder to force the blood component out of the blood bag through the liquid discharge tube. While the blood bag is pressed, a certain thickness is provided at its upper end to allow the blood component to flow out of the blood back through the blood discharge tube.

13 Claims, 13 Drawing Sheets

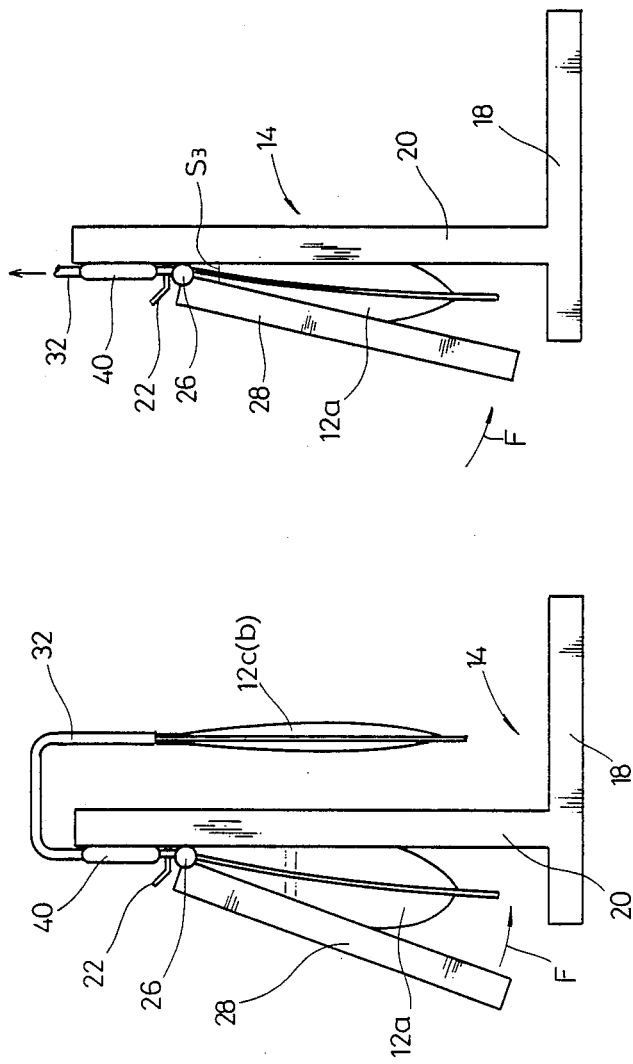

FIG.8
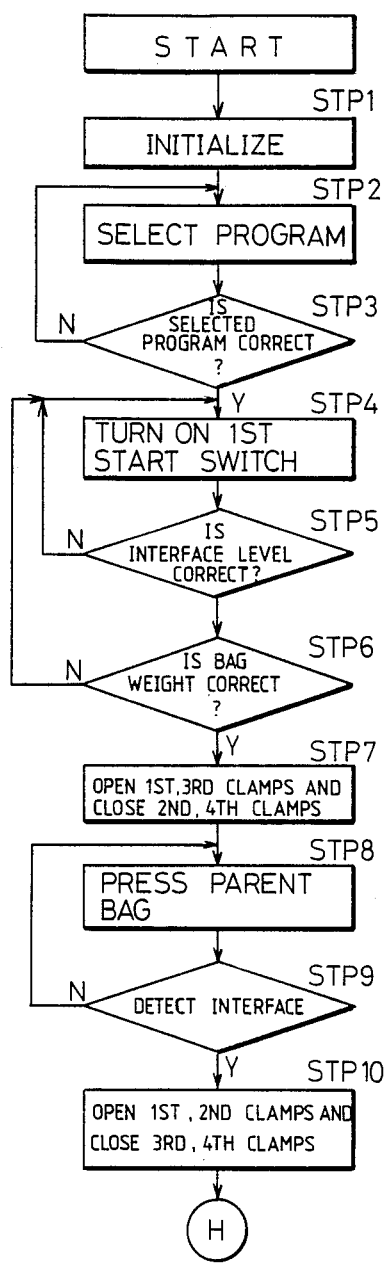
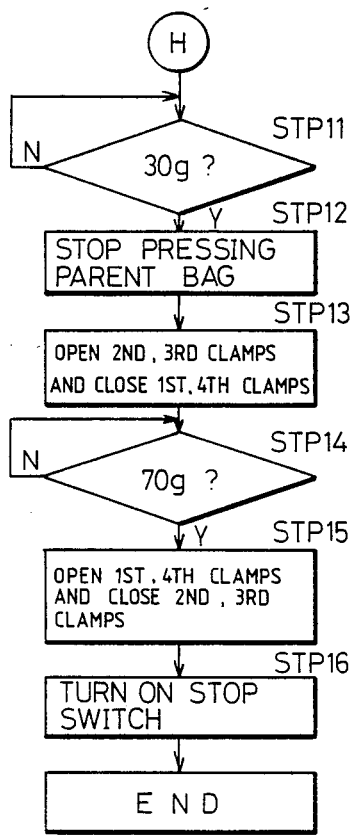

(a)

(b)

LIQUID SEPARATOR

BACKGROUND OF THE INVENTION

The present invention relates to a liquid separator, and more particularly to an apparatus for separating various blood portions or components such a blood plasma, red cells, etc. from blood stored in a flexible container such as a blood bag or the like.

It is known that conventional whole blood transfusion causes various problems particularly with respect to patients to whom blood is transfused. To avoid physical strains on the body of patients and reduce harmful immunity-related side effects, there has generally been employed component transfusion by which only a blood component required by a patient is transfused to the patient. Component preparations can be produced by separating, with a centrifugal separator, various blood components from blood stored in a blood bag, and storing the separated blood components in respective component bags.

Various devices are known for separating blood in a blood bag into blood components. These separating devices are roughly divided into two groups. According to a separating device of one group, the blood bag is locally pressed in its lower portion. A separating device of the other type presses the blood bag uniformly over its entire area.

The former blood separator is disclosed in Japanese Patent Publications Nos. 55-17585, 57-30507, and 62-502594, for example. The disclosed blood separator includes a separating stand 2a as shown FIG. 1(a) of the accompanying drawings.

Blood contained in a blood bag 4a is separated into blood components by a centrifugal separator One of the separated components, i.e., blood plasma, is then separated into a component bag (not shown) by the separating stand 2a, and thereafter, a tube 6a extending between the blood bag 4a and the component bag is sealed off by a tube sealer (not shown).

More specifically, the blood bag 4a is hung from a hook 7a on the separating stand 2a such that red cells in the blood bag 4a will not be agitated and mixed with the other separated blood components. Then, the blood bag 4a is pressed by a presser plate 9a that is angularly moved about a pivot shaft 8 in the direction indicated by the arrow A. Since the presser plate 9a is rotatably mounted on the separating stand 2a by the pivot shaft 8 that is positioned below the blood bag 4a, the lower portion of the blood bag 4a is compressed to force blood plasma out of the blood bag 4a upwardly into the component bag through the tube 6a joined to the upper end of the blood bag 4a. By continuously pressing the blood bag 4a until the interface between the blood plasma and the red cells reaches the upper end of the blood bag 4a. After the blood plasma has entirely been separated from the blood bag 4a, the tube 6a is sealed off by the tube sealer.

The latter blood separating device is known from Japanese Laid-Open Patent Publications Nos. 55-155652 and 61-29363, for example. The blood separating device employs a separating stand 2b as illustrated in FIG. 1(b) of the accompanying drawings. In operation, a blood bag 4b is hung from a hook 7b on the separating stand 2b with care exercised not to disturb separated red cells in the blood bag 4b. Then, the blood bag 4b is uniformly compressed by a presser plate 9b which is horizontally displaced toward the separating stand 2b in the direction indicated by the arrow B. Blood plasma is forced out of the blood bag 2b into a component bag (not shown) through a tube 6b.

The blood separators of the above two types may be operated either automatically or manually. If they are operated automatically, the interface between the blood plasma and the red cells in the blood bag is automatically detected by an optical interface sensor.

With the conventional blood separators, however, since the interfacial areas $S_1$, $S_2$ between the blood plasma and the red cells or a buffy coat layer in the blood bags 2a, 2b are large, any error in the detection of the interfacial position by visual inspection or the optical interface sensor induces a large error in the amount of the separated component. Accordingly, the desired blood component may not be separated with a good yield.

SUMMARY OF THE INVENTION

It is a major object of the present invention to provide a liquid separator which can precisely detect the interfaces between components of a liquid for separating the liquid components with a good yield.

Another object of the present invention is to provide a liquid separator for separating a liquid layer from a flexible container storing upper and lower liquid layers therein and having a liquid discharge tube on an upper end thereof, said liquid separator comprising: a container holder for holding the container with the liquid discharge tube directed substantially upwardly; and a container presser for providing a predetermined thickness at the upper end of the container held by said container holder and for pressing a portion of the container which has a larger thickness than said predetermined thickness, progressively from the upper end toward a lower end thereof in coaction with said container holder to force the upper liquid layer out of the container through the liquid discharge tube.

Still another object of the present invention is to provide a liquid separator wherein said container presser comprises a presser plate swingably supported at an upper end thereof on said container holder, said upper end of the presser plate and said container holder being spaced from each other by a distance which maintains said predetermined thickness at the upper end of the container.

Yet another object of the present invention is to provide a liquid separator wherein said presser plate is made of a substantially light-transmissive material.

Yet still another object of the present invention is to provide a liquid separator for separating a liquid layer from a first flexible container storing upper and lower liquid layers therein and having a liquid discharge tube on an upper end thereof, said liquid separator comprising a first container holder for holding the first container with the liquid discharge tube directed substantially upwardly; a container presser for pressing the container progressively from the upper end toward a lower end thereof to force the upper liquid layer out of the first container through the liquid discharge tube; a second container holder for holding a second flexible container for storing the upper liquid layer delivered from the liquid discharge tube through a passage; opening/closing means for selectively opening and closing said passage; an interface sensor for detecting the interface separating the upper and lower liquid layers in the first container; and a control unit for generating control signals based on a detected signal from said interface sensor and a predetermined control program stored in said control unit, and for applying said control signals to said container presser and said opening/closing means to automatically separate the upper liquid layer from said first container and deliver the upper liquid layer into said second container.

A further object of the present invention is to provide a liquid separator wherein said container presser comprises a presser plate swingably supported at an upper end thereof on said first container holder, said upper end of the presser plate and said first container holder being spaced from each other by a distance which maintains a predetermined thickness at the upper end of the first container.

A still further object of the present invention is to provide a liquid separator wherein said upper end of the presser plate is supported on said first container holder by means of a support member, further including an actuator for moving said support member toward and away from said first container holder.

A yet further object of the present invention is to provide a liquid separator wherein said presser plate is made of a substantially light-transmissive material.

A yet still further object of the present invention is to provide a liquid separator wherein said first container presser comprises a holder plate openable and closable with respect to said first container holder for holding the first container in said first container holder, an actuator, and a presser plate swingably operable by said actuator for pressing the first container progressively from the upper end to a lower end thereof in coaction with said holder plate.

Another object of the present invention is to provide a liquid separator wherein upper ends of said holder and presser plates are spaced from each other by a distance which maintains a predetermined thickness at the upper end of said first container.

Still another object of the present invention is to provide a liquid separator wherein said holder plate is made of a substantially light-transmissive material.

A further object of the present invention is to provide a liquid separator wherein said passage comprises tubes connected respectively to the first and second containers, said opening/closing means comprising clamp means for selectively opening and closing said tubes, respectively, and solenoids for operating said clamp means, respectively, to open and close said tubes.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 3 is a side elevational view of the liquid separator shown in FIG. 2;

FIG. 4 is a side elevational view of the liquid separator, showing the manner a blood bag is pressed;

FIG. 8 is a flowchart of an operation sequence of the automatic liquid separator with a quadruple-bag type blood bag set for removing leukocytes from blood that has been subjected to a first centrifugal separation process;

DETAILED DESCRIPTION OF THE PREFERRED EMBODIMENTS

Figure 2:
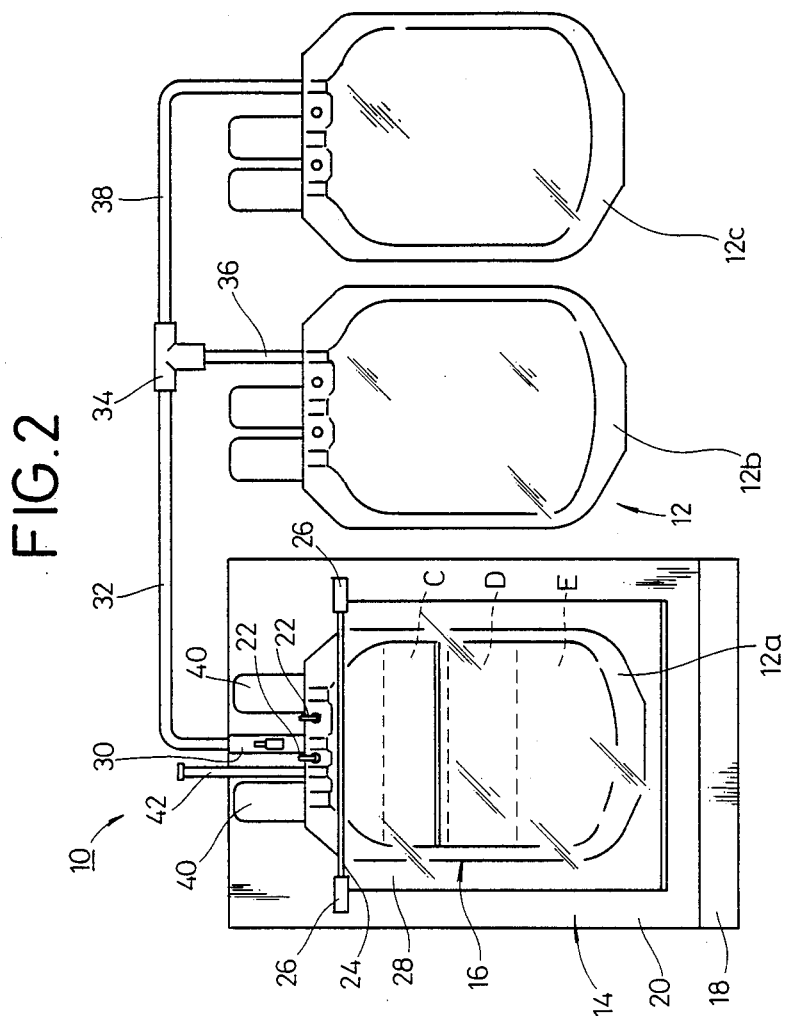
FIG. 2 is a front elevational view of a liquid separator according to a first embodiment of the present invention, with a triple-bag type blood bag set connected thereto.

As shown in FIGS. 2 through 4, a liquid separator 10 according to a first embodiment of the present invention is basically constructed of a container holder 14 for holding a blood bag set 12 including flexible containers or blood bags, and a container presser 16 for cooperating with the container holder 14 in pressing the blood bag 12 held by the container holder 14. In the illustrated embodiment, the blood bag set 12 is of a triple-bag type including a parent bag 12a, a first child bag 12b, and a second child bag 12c.

The container holder 14 has a rectangular horizontal plate 18 and a rectangular vertical plate 20 mounted on the horizontal plate 18. Two hooks 22 are attached to an upper portion of the vertical plate 20 for hanging the parent bag 12a. The container presser 16 has a horizontal pivot shaft 24 angularly movably supported on the vertical plate 20 beneath the hooks 22 by means of support members 26 on opposite ends of the pivot shaft 24. The pivot shaft 24 is positioned near the upper end of the parent bag 12a which is hung from the hooks 22. A presser plate 28 of a transparent material is joined at its upper end to the pivot shaft 24 and depends downwardly. The upper end of the presser plate 28 is spaced a certain distance from the upper end of the parent bag 12a hanging from the hooks 22. The distance between the upper ends of the presser plate 28 and the parent bag 12a is selected to allow the upper end of the parent gag 12a to have a certain thickness so that separated blood components stored in the parent bag 24 can pass through the upper end of the parent bag 24.

A liquid discharge tube 30 having a rupturable and removable plug is joined to the upper end of the parent bag 12. The liquid discharge tube 30 is connected to the first child bag 12b through a tube 32, a T-branch tube 34, and a tube 36, and also to the second child bag 12c through the tube 32, the T-branch tube 38, and a tube 38. The parent bag 12a has on its upper end a pair of discharge ports 40 and a tube 42 connected to a blood sampling needle (not shown).

The liquid separator of the first embodiment is basically constructed as described above. Operation and advantages of the liquid separator will be described below.

As shown in FIG. 2, a triple-bag type blood bag set 12 including parent and child bags 12a, 12b, 12c is employed, and 400 ml of blood is sampled from a blood donor into the parent bag 12a through the blood sampling needle joined to the parent bag 12a. Thereafter, the blood bag set 12 is set in a centrifugal separator (not shown) to separate the sampled blood in the parent bag 12a into a plasma layer C, a buffy coat layer D, and a red cell layer E therein.

Then, the parent bag 12a with the centrifugally separated blood portions or components is hung from the hooks 22 of the container holder 1. The presser plate 28 is turned in the direction indicated by the arrow (FIG. 3) to press the parent bag 12a. At this time, a portion of the parent bag 12a which has a thickness larger than the thickness of the upper end of the parent bag 12a is pressed by the presser plate 28. The upper plasma layer C in the parent bag 12a is therefore forced out of the parent bag 12a through the liquid discharge tube 30 into the first child bag 12b. When the interface between the plasma layer C and the buffy coat layer D reaches the junction between the liquid discharge tube 30 and the parent bag 12a, the parent bag 12a is depressurized, and the liquid discharge tube 30 is closed off by a clamp (not shown).

Figure 1B:
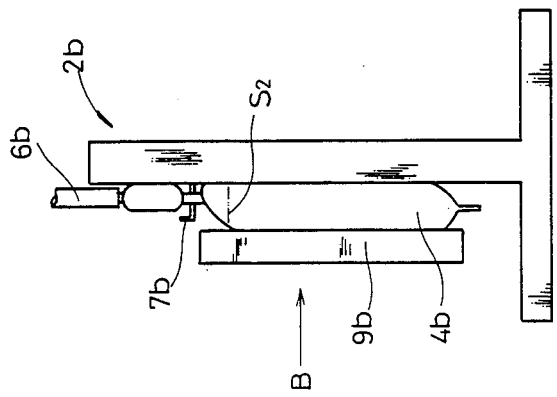
FIGS. 1(a) and 1(b) are side elevational views of conventional liquid separators, showing the manner in which blood bags are pressed.
Figure 1A:
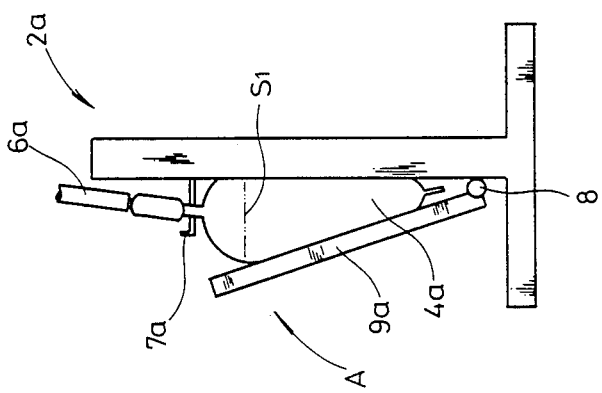

At this time, as shown in FIG. 4, since the cross-sectional area $S_3$ of the parent bag 12a near the liquid discharge tube 30 is smaller than those of the blood bags in the conventional liquid separators shown in FIGS. 1(a) and 1(b) ($S_1 > S_2 > S_3$), the amount of blood plasma remaining in the parent bag 12a is small, and hence the blood plasma can be separated with high accuracy from the parent bag 12a.

Thereafter, the clamp on the liquid discharge tube 30 is released, and the parent bag 12a is further pressed to transfer the buffy coat layer D from the parent bag 12a into the second child bag 12c. When the interface between the buffy coat layer D and the red cell layer E reaches the junction between the liquid discharge tube 30 and the parent bag 12a, the pressurization of the parent bag 12a is stopped, and the liquid discharge tube 30 is closed off by the clamp. At this time, the cross-sectional area of the parent bag 12a in the vicinity of the liquid discharge tube 30 is very small, and the pressure applied to the parent bag 12a near the liquid discharge tube 30 by the container presser 16 is stronger than those applied in the conventional liquid separators shown in FIGS. 1(a) and 1(b). Therefore, the buffy coat layer D is not led to the discharge ports 40 but forcibly discharged into the liquid discharge tube 30, so that the buffy coat layer D can be separated highly accurately from the parent bag 12a. As a result, the desired blood portions can be separated easily and highly accurately.

A liquid separator according to a second embodiment of the present invention will be described below with reference to FIGS. 5 through 9. Those components of the liquid separator according to the second embodiment which are identical to those of the first embodiment are denoted by identical reference numerals, and will not be described in detail.

Figure 5:
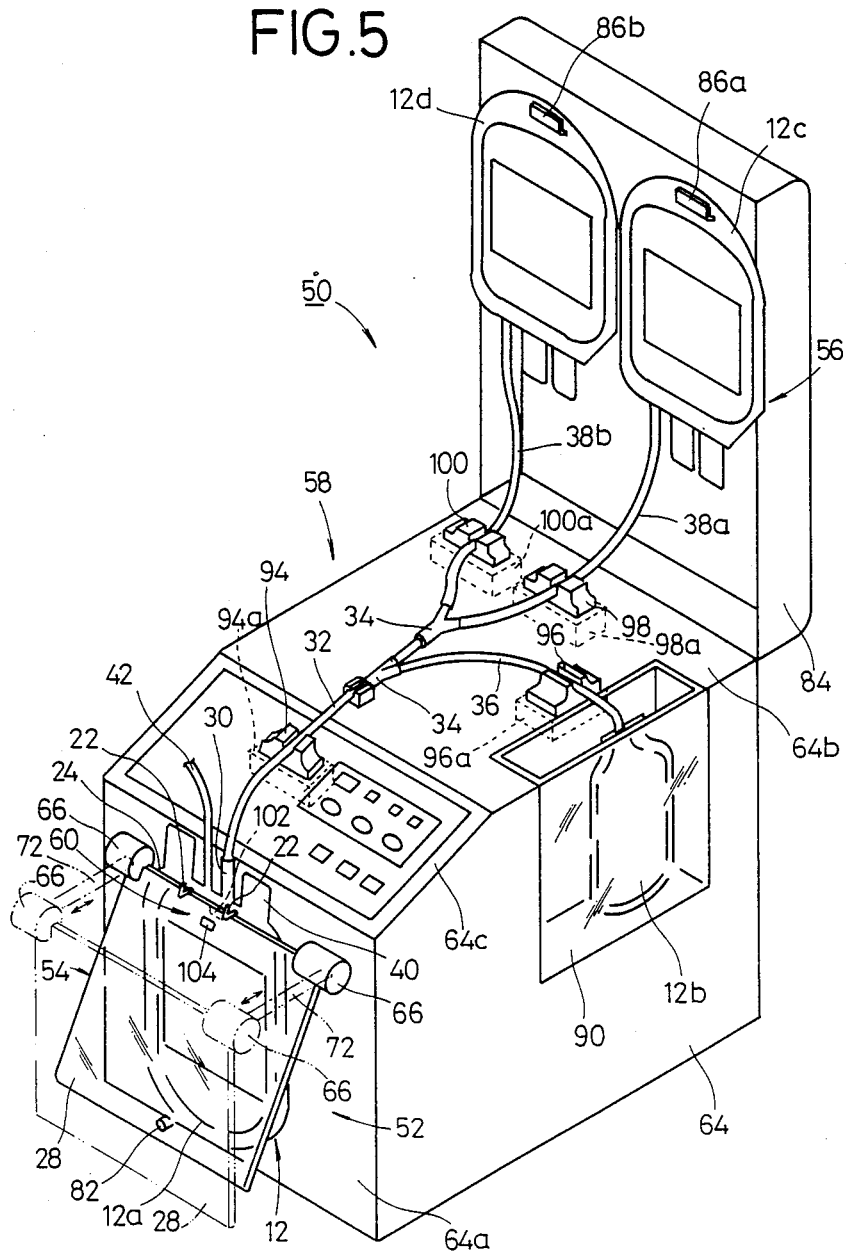
FIG. 5 is a perspective view of an automatic liquid separator according to a second embodiment of the present invention.

FIG. 5 shows an automatic liquid separator 50 which is used mainly for separating blood portions or components. A blood bag set 12 for use with the automatic liquid separator 50 may be of a double-bag type including a bag for storing 200 ml of a blood component and a bag for storing 400 ml of a blood component, of a triple-bag type, or of a quadruple-bag type (with or without an additive solution) for removing leukocytes.

In the illustrated second embodiment, a 400 ml quadruple-bag type blood bag set (with an additive solution) for removing leukocytes is used in combination with the automatic liquid separator 50.

Figure 6:
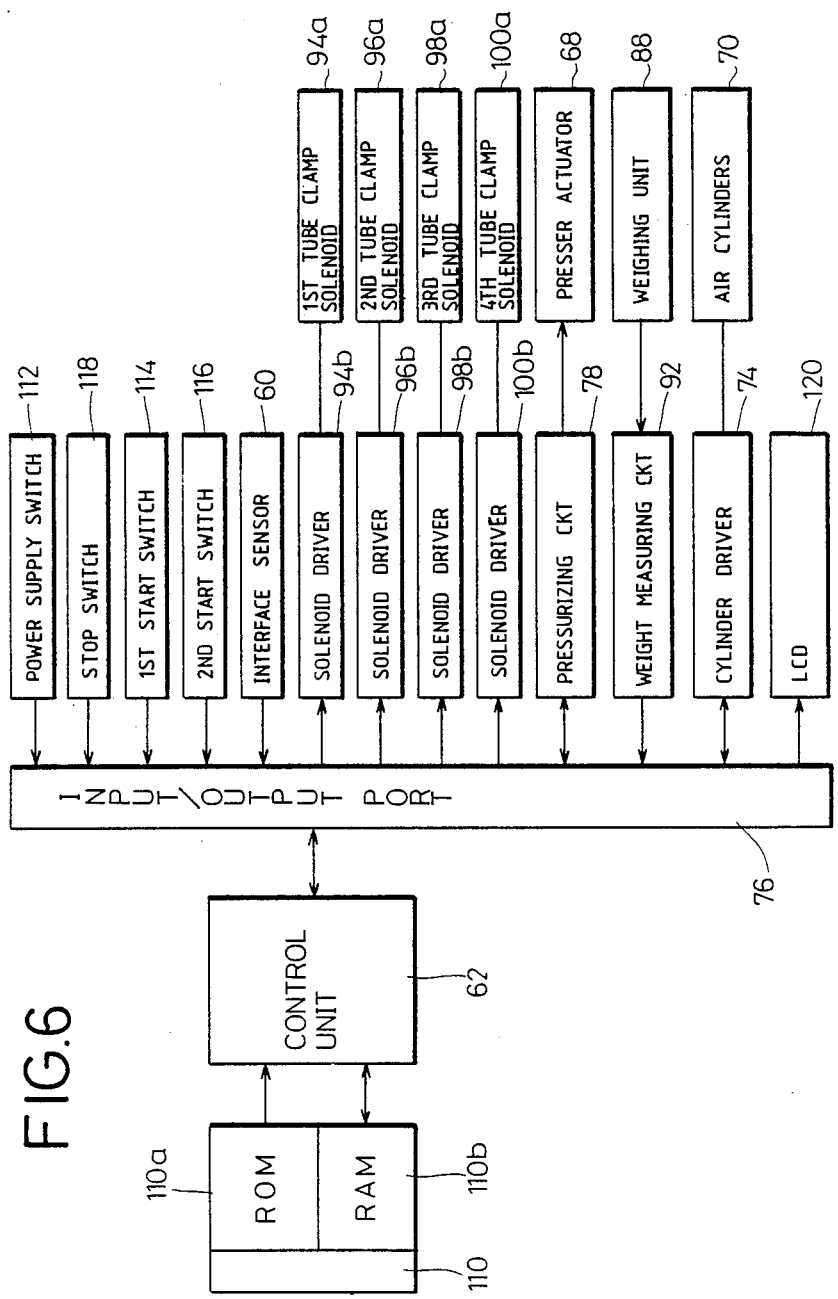
FIG. 6 is a block diagram of the automatic liquid separator shown in FIG. 5.

The automatic liquid separator 50 basically comprises a first container holder 52 for holding a parent bag 12a with a liquid discharge tube 30 joined thereto, a container presser 54 for pressing the parent bag 12a held by the first container holder 52 to push upper blood component layers out of the parent bag 12a, a second container holder 56 for holding first, second, and third child bags 12b, 12c, 12d which are supplied with the upper blood component layers from the liquid discharge tube 30 through tubes 32, 36, 38a, 38b, a tube opening/closing assembly 58 for selectively opening and closing the tubes 32, 36, 38a, 38b, an interface sensor 60 for detecting interfacial boundaries between the component layers in the parent bag 12a, and a control unit 62 for generating control signals to operate the container presser 54 and the tube opening/closing assembly 58 based on a detected signal from the interface sensor 60 and a predetermined control program (see FIGS. 5 and 6).

The first container holder 52 is positioned on one side wall 64a of a housing 64 and has two hooks 22 for hanging the parent bag 12a.

Figure 7A:
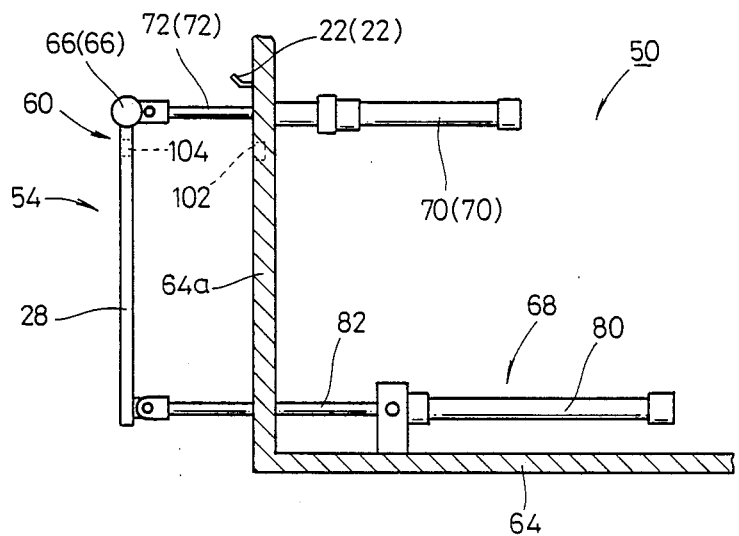
FIGS. 7(a), 7 (b), and 7(c) are schematic views illustrating the manner in which the automatic liquid separator operates.
Figure 7B:
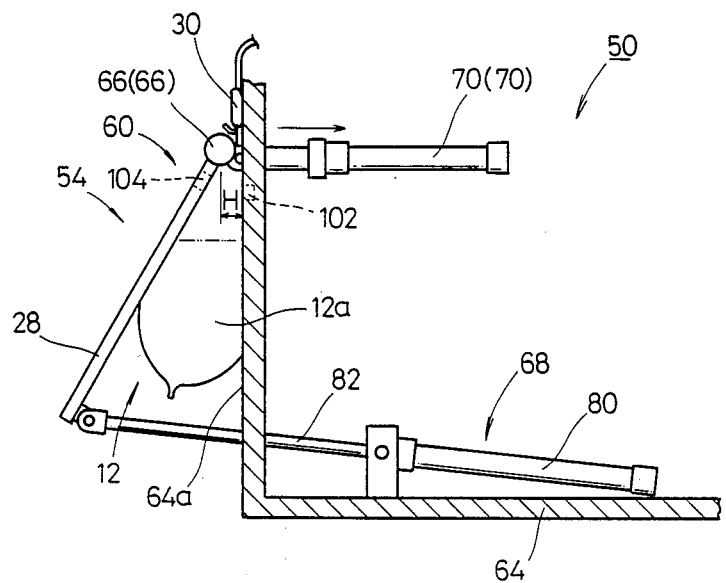
Figure 7C:
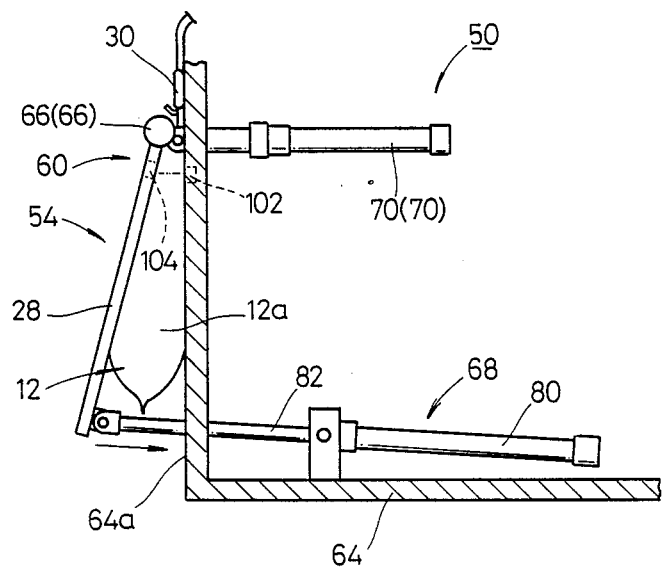

The container presser 54 comprises a pivot shaft 24, a presser plate 28 fixed to the pivot shaft 24, two support members 66 mounted on an upper portion of the side wall 64a of the housing 64 and supporting the pivot shaft 24, the support members 66 being spaced a certain distance from the side wall 64a, and a presser actuator 68 (FIGS. 7(a) through 7(c)) for angularly moving the presser plate 28. As illustrated in FIGS. 7(a) through 7(c), a pair of air cylinders 70 is supported on an upper portion of the side wall 64a and housed in the housing 64. The air cylinders 70 have respective piston rods 72 exposed out of the housing 64 and connected to the support members 66, respectively. As shown in FIG. 6, the air cylinders 70 are electrically connected to the control unit 62 through a cylinder driver 74 and an input/output port 76.

The presser actuator 68 is disposed in the housing 64 and electrically connected to the control unit 62 through a pressurizing circuit 78 and the input/output port 76. The presser actuator 68 comprises an air cylinder 80, for example, swingably mounted in the housing 64 and having a piston rod 82 connected to a lower end of the presser plate 28. The presser actuator 68 may comprise a spring motor, a hydraulic cylinder, or the like.

The second container holder 56 has a lid 84 openably and closably hinged to the upper surface 64b of the housing 64. The lid 84 can be fixed in a vertical direction normal to the upper surface 64b. The lid 84 has hooks 86a, 86b for hanging the child bags 12c, 12d. The housing 64 has a side chamber 90 for storing the child bag 12b therein, the chamber 90 housing a hanger-type weighing unit 88. The weighing unit 88 is electrically connected to the control unit 62 through a weight measuring circuit 92 and the input/output port 76 (FIG. 6).

The tube opening/closing assembly 58 comprises a first tube clamp 94 mounted on a slanted surface 64c of the housing 64, and second, third, and fourth tube clamps 96, 98, 100 mounted on the upper surface 64b. The tube clamps 94 through 100 can be selectively opened and closed by respective solenoids 94a, 96a, 98a, 100a which are electrically connected to the control unit 62 through respective solenoid drivers 94b, 96b, 98b, 100b and the input/output port 76.

The interface sensor 60 serves to detect the interface between a plasma layer C and a buffy coat layer D and the interface between the buffy coat layer D and a red cell layer E in the blood bag 12a. The interface sensor 60 generally comprises a photosensor. More specifically, the interface sensor 60 includes a light-emitting element 102 mounted on an upper portion of the side wall 64a and a light detector element 104 mounted on an upper portion of the presser plate 28. An interface between blood component layers can be detected based on the different light absorption coefficients of the blood component layers when light emitted from the light-emitting element 102 is detected by the light detector element 104. The position of the interface sensor 60 can be vertically adjusted. The interface sensor 60 is electrically coupled to the control unit 62 through the input/output port 76.

The control unit 62 processes various signals supplied through the input/output port 76 and information read from a memory unit 110 including a ROM 110a and a RAM 110b to generate and apply control signals through the input/output port 76 and the drivers and circuits to the respective actuating elements. The ROM 110a stores control programs representing control sequences according to the present invention, and is electrically conneCted to the control unit 62. The control sequences represented by the control programs are effective in separating blood components from blood in amounts of 400 ml, 200 ml, etc. The control programs can be selected by operating a selector switch. Alternatively, program cassettes storing respective control programs may be replaced to select desired control programs.

To the control unit 62, there are also electrically connected a power supply switch 112, a first start switch 114, a second start switch 116, a stop switch 118, and a liquid crystal display (LCD) 120 through the input/output port 76. These switches are mounted on a panel on the slanted surface 64c of the housing 64. The liquid crystal display 120 is mounted on a control panel on the housing 64. The liquid crystal display 120 can display the title of a control program being selected and executed, so that the operator can confirm whether the presently selected control program is proper. Any error message, e.g., indicating that the interface level is abnormal or the weighing unit 88 is malfunctioning (such as when a child bag is not set in place), is also displayed on the liquid crystal display 120.

Operation and advantages of the automatic liquid separator thus constructed will be described below.

FIG. 8 shows a control sequence of the automatic liquid separator 50 at the time a quadruple-bag type blood bag set 12 for removing leukocytes from centrifugally separated blood is used in combination with the automatic liquid separator 50.

The power supply switch 112 of the automatic liquid separator 50 is turned on to initialize the control unit 62 in a step 1. A blood bag set 12 of the quadruple-bag type containing in its parent bag 12a 400 ml of blood donated from a blood donor is subjected to centrifugal separation for 5 minutes with centrifugal forces ranging from 3,000 G to 4,000 G. The blood bag set 12 with its blood centrifugally separated into blood components is then set in the automatic liquid separator 50, as shown in FIG. 5. More specifically, as shown in FIG. 7(a), the air cylinders 70 are operated to cause the piston rods 72 to project the support members 66 and the presser plate 28 as indicated by the dotted lines. Thereafter, the parent bag 12a storing 400 ml of centrifugally separated whole blood is hung from the hooks 22 of the first container holder 52. The air cylinders 70 are operated again to displace the presser plate 28 toward the side wall 64a to a position where there is a distance or gap H remaining between the upper end of the presser plate 28 and the upper end of the side wall 64a (see FIG. 7(b)). The first child bag 12b is placed in the chamber 90 of the second container holder 56, and the second and third child bags 12c, 12d are hung from the hooks 86a, 86b, respectively, on the lid 84.

The tube 32 of the blood bag set 12 is set in the first tube clamp 94, the tube 36 in the second tube clamp 96, the tubes 38a, 38b in the third and fourth tube clamps 98, 100, respectively.

After the blood bag set 12 has been set in the automatic liquid separator 50, a control program for the quadruple-bag type blood bag set is selected and read out of the memory unit 110 in a step 2. The title of the selected and read control program is now displayed on the liquid crystal display 120. The operator looks at the displayed program title, and determines whether the displayed control program is correct for the type of the blood bag set in a step 3. If the displayed program is incorrect, then the stop switch 118 is turned on to cancel the selected control program, and control goes back to the step 2 where a correct control program is selected and read out again. If the displayed control program is correct, then control proceeds to a step 4 in which the first start switch 114 is turned on, and then control goes to a step 5.

The step 5 determines whether a interface level between blood component layers is in a predetermined position, i.e., whether the parent bag 12a is set in place or not. This decision step 5 is performed by the operator who sees the interface level displayed on the liquid crystal display 120. If the interface level is not in the predetermined position, then the operator turns on the stop switch 118, sets the parent bag 12a again, and then turns on the first start switch 114 again. If the interface level is in the predetermined position, then control goes to a step 6 in which the operator determines whether the weight measured by the weighing unit 88 is a predetermined weight, i.e., whether the first child bag 12b is set in place, by looking at the weight displayed on the liquid crystal display 120. If the displayed weight is wrong, then the first child bag 12b is set in position, and the first start switch 114 is turned on again. If the displayed weight is correct, then the first and third tube clamps 94, 98 are opened and the second and fourth clamps 96, 100 are closed in a step 7.

The step 7 is followed by a step 8 in which the air cylinder 80 is operated to turn the presser plate 28 about the pivot shaft 24 to start pressing the parent bag 12a (see FIG. 7(c)). At this time, the plug in the liquid discharge tube 30 of the parent bag 12a is broken and removed to bring the parent bag 12a and the tube 32 into fluid communication with each other. The plasma layer C in the parent bag 12a now starts to be transferred into the second child bag 12c.

Then, the interface between the plasma layer C and the buffy coat layer D in the parent bag 12a is checked to see if the interface has reached a predetermined position in a step 9. If the interface has not yet reached the predetermined termined position, then the parent bag 12a is continuously pressed by the presser plate 28 to feed the plasma layer C into the second child bag 12c. If the interface has reached the predetermined position, then control goes to a step 10 in which the first and second tube clamps 94, 96 are opened, and the third and fourth tube clamps 98, 100 are closed, to transfer a portion of the plasma layer D and portions of the buffy coat layer D and the red cell layer E into the first child bag 12b.

Then, a step 11 determines whether the weight of the blood components in the first child bag 12b has reached 30 g or not. If not, then control waits until the weight of the blood components in the first child bag 12b reaches 30 g. If the weight has reached 30 g, then control proceeds to a step 12 in which the pressurization of the parent bag 12a is stopped. In a next step 13, the second and third tube clamps 96, 98 are opened, and the first and fourth tube clamps 94, 100 are closed. Therefore, the plasma layer C stored in the second child bag 12c flows by gravity into the first child bag 12b. Then, a step 14 determines whether the weight of the blood components in the first child bag 12b has reached 30 g+40 g=70 g or not. If not, control waits until the weight reaches 70 g.

If the weight has reached 70 g, then the first and fourth tube clamps 94, 100 are opened and the second and third tube clamps 96, 98 are closed in a step 15. These tube clamps remain opened and closed for a prescribed period of time. A rupturable and separable plug in the tube 38b connected to the third child bag 12d is broken and removed to allow an additive solution for preserving red cells to be transferred from the third child bag 12d into the parent bag 12a.

After the condition of the step 15 has continued for the prescribed period of time, control proceeds to a step 16 in which the stop switch 118 is turned on and the power supply switch 112 is turned off to complete the cycle of separating the blood components from blood which has been subjected to a first centrifugal separation process. Thereafter, the tubes 32, 38a are sealed off by a tube sealer (not shown), and the parent bag 12a and the second child bag 12c are cut off from the other bags, and stored in a given place.

Figure 9:
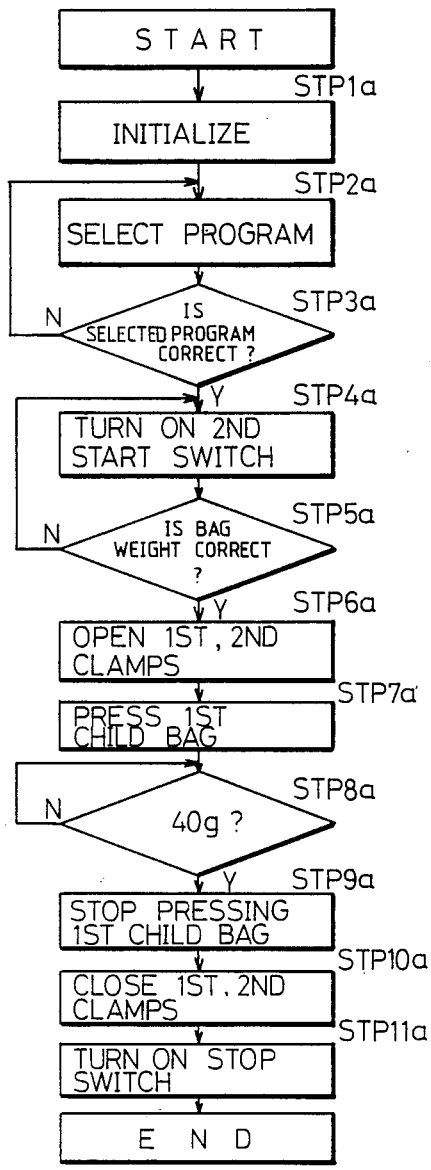
FIG. 9 is a flowchart of an operation sequence of the automatic liquid separator after a second centrifugal separation process.

FIG. 9 shows an operation sequence for separating blood components from the first and third child bags 12b, 12d which have been subjected to a second centrifugal separation process, e.g., for 5 minutes with centrifugal forces ranging from 150 G to 200 G.

The power supply switch 112 is turned on to initialize the control unit 62 in a step 1a. Then, the first and third child bags 12b, 12d are set in the automatic liquid separator 50. More specifically, the first child bag 12b is hung from the hooks 22 of the first container holder 52, and the third child bag 12d is placed in the chamber 90 of the second container holder 56 and hung from the hanger of the weighing unit 88. The tube 32 of the blood bag set is set in the first tube clamp 94, and the tube 38b in the second tube clamp 96.

After the first and second child bags 12b, 13b have been set in the automatic liquid separator 50, a control program for the child bags having been subjected to the second centrifugal separation process is selected and read out of the memory unit 110 in a step 2a. The title of the selected and read control program is now displayed on the liquid crystal display 120. The operator looks at the displayed program title, and determines whether the displayed control program is correct for the child bags in a step 3a. If the displayed program is incorrect, then the stop switch 18 is turned on to cancel the selected control program, and control goes back to the step 2a where a correct control program is selected and read out again. If the displayed control program is correct, then control proceeds to a step 4a in which the second start switch 116 is turned on, and then control goes to a step 5a.

The step 5a determines whether the weight measure by the weighing unit 88 is a predetermined weight, i.e., whether the third child bag 12d is set in place, by looking at the weight displayed on the liquid crystal display 120. If the displayed weight is wrong, then the stop switch 118 is turned on, the third child bag 12d is set in position, and the second start switch 116 is turned on again. If the displayed weight is correct, then the first and second tube clamps 94, 96 are closed in a step 6a.

Then, control proceeds to a step 7a in which the presser plate 28 is turned to start pressing the first child bag 12b. A rupturable and separable plug in the tube 36 connected to the first child bag 12b is broken and removed to allow platelets to be transferred from the first child bag 12b into the third child bag 12d. Then, a step 8a determines whether the weight of platelets in the third child bag 12d has reached 40 g or not. If not, control waits until the weight reaches 40 g. If the weight of platelets has reached 40 g, then the presser plate 28 stops pressing the first child bag 12b in a step 9a, and then the first and second tube clamps 94, 96 are closed in a step 10a. The step 10a is followed by a step 11a in which the stop switch 118 is turned on and the power supply switch 112 is turned off to complete the cycle of separating the platelets from the blood components which have been subjected to the second centrifugal separation process. Thereafter, the tube 36 or 38b is sealed off by a tube sealer (not shown), and the first and third child bags 12b, 12d are cut off from each other.

The first child bag 12b is discarded, and the third child bag 12d is stored in a given place.

An automatic liquid separator 50a according to a third embodiment will hereinafter be described with reference to FIGS. 10, 11(a), and 11(b). Those parts of the automatic liquid separator 50a which are identical to those of the automatic liquid separator 50 illustrated in FIGS. 5 through 7 are designated by identical reference numerals, and will not be described in detail.

The automatic liquid separator 50a has a holder plate 130 of a transparent material which is swingably supported at its lower end on the side wall 64a of the housing 64. The holder plate 130 openably closes a recess 132 defined in the side wall 64a. As illustrated in FIGS. 11(a) and 11(b), a container presser 54a is disposed in the housing 64. The container presser 54a includes a presser plate 134 swingably mounted at its upper end on the upper panel of the housing 64. A presser actuator 68a comprises an air cylinder 136 mounted on the lower panel of the housing 64 having a piston rod 138 joined at its tip end to the lower end of the presser plate 134. An interface sensor 60a comprises a light-emitting element 102a attached to an upper portion of the presser plate 134 and a light detector element 104a mounted on an upper portion of the holder plate 130 in substantial horizontal alignment with the light-emitting element 102a.

Figure 10:
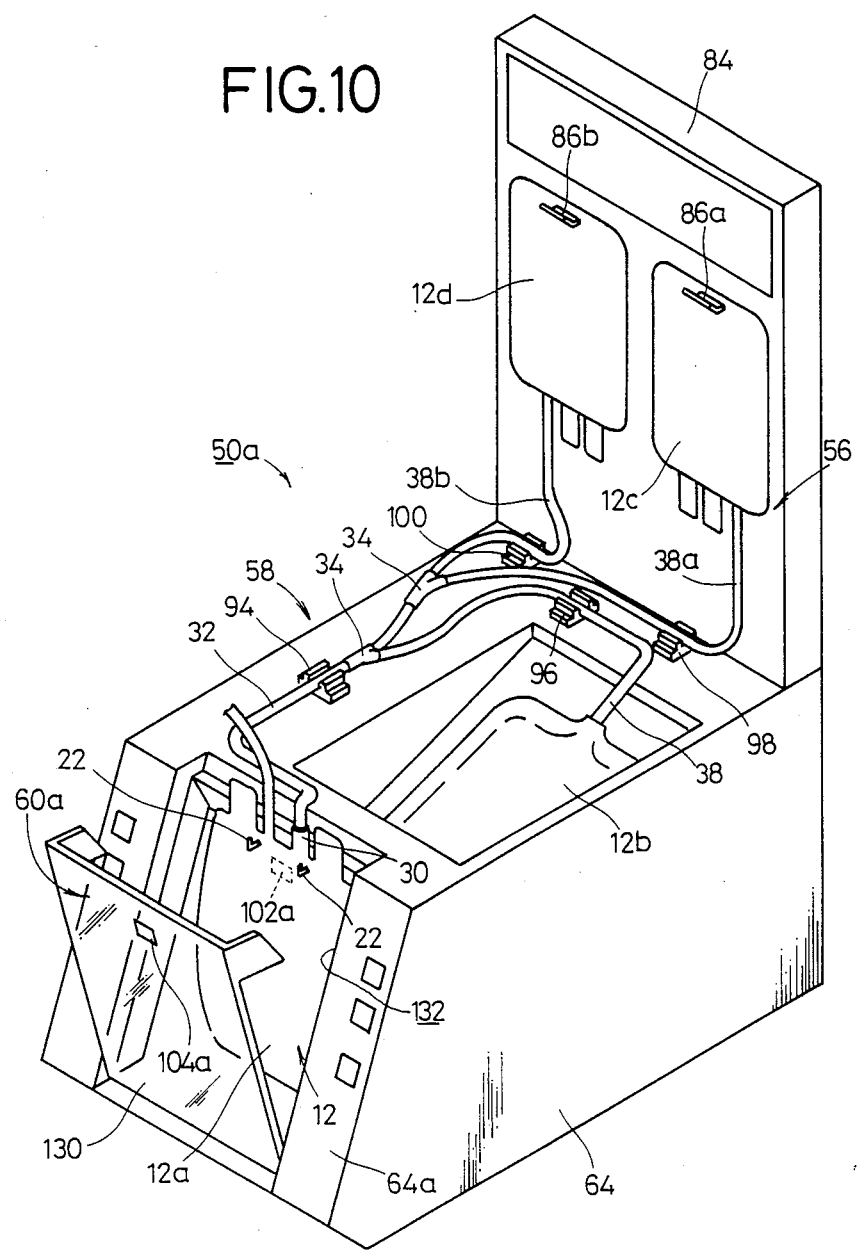
FIG. 10 is a perspective view of an automatic liquid separator in accordance with a third embodiment of the present invention.
Figure 11:
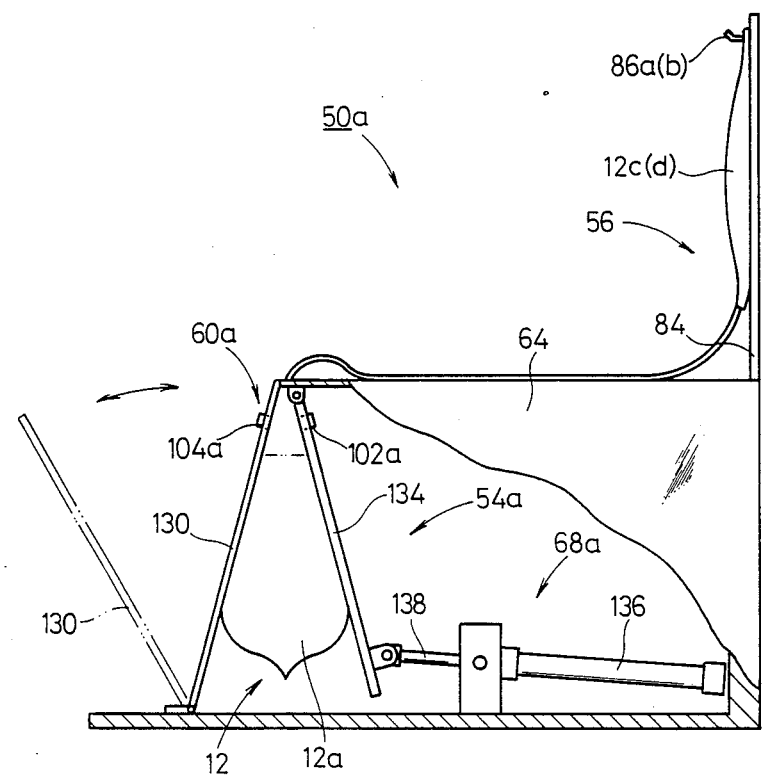
FIGS. 11(a) and 11(b) are schematic views showing operation of the automatic liquid separator of FIG. 10.
Figure 11:
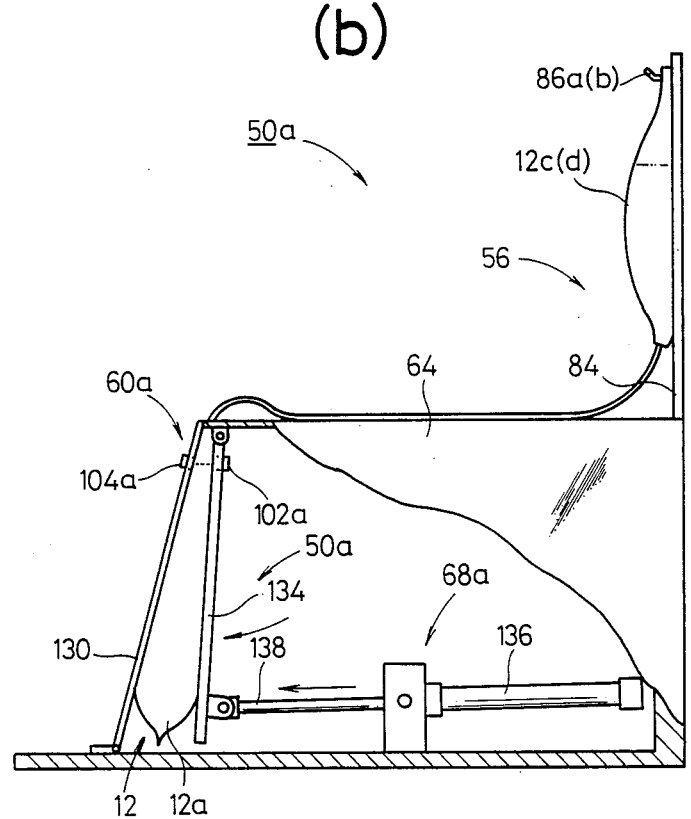

In operation, the holder plate 130 is first turned away from the recess 132 as shown in FIG. 10, and a parent bag 12a of a blood bag set 12 is placed in the recess 132 and hung from hooks 22. Then, the holder plate 130 is closed over the parent bag 12a as shown in FIG. 11(a). Then, as shown in FIG. 11(b), the air cylinder 136 is operated to turn the presser plate 134 toward the holder plate 130 to press the parent bag 12a for forcing a desired blood component or portion out of the parent bag 12a.

With the present invention, as described above, the flexible container held by the container holder with a certain thickness left at its upper end is pressed progressively downwardly by the container presser for forcibly discharging an upper liquid layer, separated by an interface from a lower liquid layer in the container, gradually through the liquid discharge tube joined to the upper end of the container. Since the container is pressed progressively downwardly, the cross-sectional area of the container near the liquid discharge tube is small, and the amount of the upper liquid layer in the container near the liquid discharge tube is also small. Therefore, the upper liquid layer can be separated easily and highly accurately from the container. Consequently, various components of a liquid contained in the container can be separated forcibly and highly accurately with a high yield.

According to the automatic liquid separator, the control unit generates control signals based on a detected signal from the interface sensor which detects the interface between upper and lower liquid layers and also based on a predetermined control program, and applies the control signals to operate the container presser and the tube opening/closing assembly. The upper liquid layer, separated by the interface from the lower liquid layer in the container, is automatically transferred through the liquid discharge tube into another container until the interface is detected by the interface sensor. Therefore, various components of a liquid can be separated forcibly and highly accurately with a high yield without requiring much experience and skill on the part of the operator.

Although certain preferred embodiments have been shown and described, it should be understood that many changes and modifications may be made therein without departing from the scope of the appended claims.

What is claimed is:

1. A liquid separator for separating a liquid layer from a flexible container storing upper and lower liquid layers therein and having a liquid discharge tube on an upper end thereof, said liquid separator comprising:
   a container holder means for holding the container with the liquid discharge tube directed substantially upwardly; and
   a container presser means for providing a space having a predetermined thickness to accommodate therein the upper end of the container held by said container holder, and for pressing a portion of the container which has a larger thickness than said predetermined thickness, progressively from the upper end toward a lower end thereof in coaction with said container holder means while maintaining said predetermined thickness of the space, to force the upper liquid layer out of the container through the liquid discharge tube.

2. A liquid separator according to claim 1, wherein said container presser comprises a presser means plate swingably supported at an upper end thereof on said container holder means, said upper end of the presser plate and said container holder means being spaced from each other to define said opening by a distance which maintains said predetermined thickness at the upper end of the container.

3. A liquid separator according to claim 2, wherein said presser plate is made of a substantially light-transmissive material.

4. A liquid separator for separating a liquid layer from a first flexible container storing upper and lower liquid layers therein and having a liquid discharge tube on an upper end thereof, said liquid separator comprising:
   a first container and a second container, with said first container being flexible so as to expand its interior volume to store a quantity of liquid therein;
   a first container holder means for holding the first container with the liquid discharge tube directed substantially upwardly;
   a container presser means for pressing the first container progressively from an upper end toward a lower end thereof to force the upper liquid layer out of the first container through the liquid discharge tube;
   a second container holder means for holding said second container for storing the upper liquid layer delivered from the liquid discharge tube through a passage;
   opening/closing means for selectively opening and closing said passage;
   an interface sensor means for detecting an interface separating the upper and lower liquid layers in the first container; and
   a control unit means for generating control signals based on a detected signal from said interface sensor means and a predetermined control program stored in said control unit means, and for applying said control signals to said container presser means and said opening/closing means to automatically separate the upper liquid layer from said first container and deliver the upper liquid layer into said second container.

5. A liquid separator according to claim 4, wherein said container presser means comprises a presser plate swingably supported at an upper end thereof on said first container holder means, said upper end of the presser plate and said first container holder means being spaced from each other by a distance of a predetermined thickness and accommodating therebetween the upper end of the first container, and which distance is maintained substantially unchanged despite motion of said presser plate.

6. A liquid separator according to claim 5, wherein said upper end of the presser plate is supported on said first container holder means by means of a support member, further including an actuator means for moving said support member toward and away from said first container holder means.

7. A liquid separator according to claim 6, said pressure plate is made of a substantially light-transmissive material.

8. A liquid separator according to claim 5, wherein said presser plate is made of a substantially light-transmissive material.

9. A liquid separator according to claim 4, wherein said container presser means comprises a holder plate openable and closable with respect to said first container holder means for holding the first container in said first container holder means, an actuator, and a presser plate means swingably operable by said actuator for pressing the first container progressively from the upper end to a lower end thereof in coaction with said holder plate.

10. A liquid separator according to claim 9, wherein respective upper ends of said holder plate and presser plate are spaced from each other by a distance which maintains a predetermined thickness at the upper end of said first container.

11. A liquid separator according to claim 10, wherein said holder plate is made of a substantially light-transmissive material.

12. A liquid separator according to claim 9, wherein said holder plate is made of a substantially light-transmissive material.

13. A liquid separator according to claim 4, further including a passage in communication between said liquid discharge tube and said second container which comprises tubes connected respectively to the first and second containers, said opening/closing means comprising clamp means for selectively opening and closing said tubes, respectively, and solenoid means for operating said clamp means, respectively, to open and close said tubes.

* * * * *

UNITED STATES PATENT AND TRADEMARK OFFICE
CERTIFICATE OF CORRECTION

PATENT NO. : 4,976,851
DATED : December 11, 1990
INVENTOR(S) : TANOKURA et al It is certified that error appears in the above-identified patent and that said Letters Patent is hereby corrected as shown below:

Title page, Section [56] References Cited:
    Change US Patent "3,753,739 6/1968" to
    --4,753,739 6/1988--.
Column 1, line 7, change "a" to --as--.
Column 4, line 52, change "gag" to --bag--.
Column 7, line 28, change "conneCted" to --connected--.
Column 8, line 16, before "the tubes 38a", insert --and--.
Column 9, line 68 (last line), change "18" to --118--.
Column 11, line 62 (Claim 2), before "comprises", insert
    --means-- and delete "means" before "plate".
Column 12, line 46 (Claim 5), delete "substantially
    unchanged".

Signed and Sealed this

Sixth Day of October, 1992

*Attest:*

DOUGLAS B. COMER

*Attesting Officer*      *Acting Commissioner of Patents and Trademarks*